United States Patent
Huang (10) Patent No.: US 10,571,480 B2
(45) Date of Patent: Feb. 25, 2020

(54) BIOSENSORS FOR CELLULAR OSMOLARITY

(71) Applicant: Tempo Bioscience, Inc., San Fransisco, CA (US)

(72) Inventor: Angela Huang, San Mateo, CA (US)

(73) Assignee: Tempo Bioscience, Inc., San Francisco, CA (US)

( * ) Notice: Subject to any disclaimer, the term of this patent is extended or adjusted under 35 U.S.C. 154(b) by 162 days.

(21) Appl. No.: 15/949,709

(22) Filed: Apr. 10, 2018

(65) Prior Publication Data

US 2018/0299470 A1   Oct. 18, 2018

Related U.S. Application Data

(60) Provisional application No. 62/484,424, filed on Apr. 12, 2017.

(51) Int. Cl.

| | | |
|---|---|---|
| *G01N 33/84* | (2006.01) | |
| *G01N 33/68* | (2006.01) | |
| *G01N 33/566* | (2006.01) | |
| *C07K 19/00* | (2006.01) | |
| *C12N 15/79* | (2006.01) | |
| *C12N 5/079* | (2010.01) | |
| *G01N 33/50* | (2006.01) | |
| *C07K 14/705* | (2006.01) | |

(52) U.S. Cl.
CPC .......... *G01N 33/84* (2013.01); *C07K 14/705* (2013.01); *C07K 19/00* (2013.01); *C12N 5/0621* (2013.01); *C12N 15/79* (2013.01); *G01N 33/5044* (2013.01); *G01N 33/566* (2013.01); *G01N 33/6872* (2013.01); *C07K 2319/07* (2013.01); *C07K 2319/09* (2013.01); *C07K 2319/20* (2013.01); *C07K 2319/60* (2013.01); *C07K 2319/61* (2013.01)

(58) Field of Classification Search
CPC .. G01N 33/84; G01N 33/566; G01N 33/6872; C07K 19/00; C07K 2319/60
See application file for complete search history.

(56) References Cited

U.S. PATENT DOCUMENTS

| | | |
|---|---|---|
| 2014/0010861 A1 | 1/2014 | Bancel et al. |
| 2015/0307888 A1 | 10/2015 | Malphettes |
| 2016/0178635 A1 | 6/2016 | Huang |

*Primary Examiner* — Ruixiang Li
(74) *Attorney, Agent, or Firm* — Eric P. Mirabel

(57) ABSTRACT

This invention provides biosensors, cell models, and methods of their use for monitoring osmolarity. Biosensors can include targeting domains, sensing domains and reporting domains. Biosensors can be introduced into cells reprogrammed to represent experimental or pathologic cells of interest. Model cells expressing the biosensors can be contacted with putative bioactive agents to determine possible activities, including as detectors of which is pH changes, as TempoOsmo™ accomplishes.

3 Claims, 3 Drawing Sheets
(3 of 3 Drawing Sheet(s) Filed in Color)

Specification includes a Sequence Listing.

FIG. 1

LEGEND

Black bar: Control Hepes buffer (Left)
Gray Bar: 0.1mM NaCl HBSS pH 7.4 (Second from left)
Red bar: HBSS pH 3.0 (Second from right)
Blue bar: Picrotoxin 10μM (Right)

FIG. 2

LEGEND

Red lines: HBSS pH 3.0 (Uppermost)
Blue lines: Picrotoxin 10µM (Next uppermost)
Green lines: Control Hepes buffer (Next from lowest)
Gray lines: 0.1mM NaCl HBSS pH 7.4 (Lowest)

FIG. 3

LEGEND

Black bar: Control Hepes buffer (Left)
Red Bar: HBSS pH 3.0 (Second from left)
Blue bar: 0.1mM NaCl HBSS pH 7.4 (Right)

BIOSENSORS FOR CELLULAR OSMOLARITY

SEQUENCE LISTING

The instant application contains a Sequence Listing which has been submitted electronically in ASCII format and is hereby incorporated by reference in its entirety. Said ASCII copy, created on Apr. 13, 2018, is named TEMPO-OSMO_SL.txt and is 12,622 bytes in size.

BACKGROUND

Detection of voltage potentials and changes to the internal ionic environment of cells can be useful in monitoring bioactivities of cells. For example, many cells experience significant changes in internal calcium ion ($Ca^{2+}$) concentration in response to binding of a ligand to a G-protein receptor. In another aspect, certain cells experience large changes in voltage potential across membranes, e.g., in response to contact with neurotransmitters at a synapse. Such cellular changes are responsible for important functions in cells and can be indicative of the health, function, or development processes of the cells.

Cellular osmolarity is related to volume changes in the cell (sometimes called "cell swelling"). In neuroscience, cell swelling is associated with various pathological states including cerebral ischemia and trauma.

In studying osmolarity in response to products with treatment potential, signal transduction studies are carried out in cell types that are not representative of the actual cells of interest. For example, researchers may be limited to studying signaling agents and potential therapeutics in rodents or immortal cell lines in vitro, which often provide results not repeated in human cells, or clinical patients. Researchers may create host cells for study by introduction of oncogenes to primary cell lines, e.g., with differentiation to a cell type of choice. However, such host cells or cells generated cannot be relied on to respond normally on contact with bioactive agents.

A need therefor exists for model cell systems representative of cells and tissues existing in live animal systems of interest. It would be desirable to have osmolarity sensor peptide constructs that can be targeted to specific intracellular locations. Benefits would also be realized if systems were available allowing three dimensional signal detection in mock tissues of representative cells in vitro. These systems would be useful for screening and identifying and confirming efficacy of bioactive agents.

SUMMARY

The biosensors of the invention are capable of detecting cellular water fluctuations, and as a by-product, detecting cellular "volume" (whether the cell membrane expands or shrinks). They can be used, e.g., in human iPSCs-derived cell types to image 2D or 3D cellular models of cells expressing certain pathologies. Such models can be useful in screening and evaluation of candidate drug compounds for chemical, biologic, therapeutic, and toxicological effects in humans or in other mammalian species (including companion animals e.g., dogs and cats, and livestock).

The biosensors can have structures targeting cellular compartments, e.g., the nucleus, cytoplasm, plasma, certain membrane surfaces, and/or the like. They can evaluate and report fluctuations in cell swelling or osmolarity fluctuations. TempoOsmo™ (described below) is preferably used as a nuclear and cytosolic biosensor.

The biosensors can be configured or genetically modified to contain promoter sequences specific to certain cell types, e.g., dopaminergic neurons, GABAergic neurons, astrocytes, cardiomyocytes, immortalized human cancer cell lines, HSCs, NPCs, human or mammalian cells in general and/or MSCs.

In one embodiment, the osmolarity biosensor is a peptide construct including an osmolarity sensing domain (which incorporates a transmembrane domain) and a reporter domain. The transmembrane domain is preferably adapted to integrate into a membrane of a human cell.

The reporter domain is preferably a fluorescent reporter domain. The fluorescent reporter may fluoresce at wavelengths in the range from 500 nm to 1400 nm, and preferably has a fluorescent emission range of 500 nm-700 nm and a fluorescent excitation range of 400 nm-700 nm. The biosensor may preferably change conformation (e.g., when the osmolarity sensing domain is activated), resulting in the fluorescent reporter domain changing its fluorescent emission characteristics.

In certain embodiments of the osmolarity sensing domain is a sensor peptide at least 70%, 80%, 90%, 95%, 98%, or 99% identical to:

```
                                             (SEQ ID NO: 1)
MSDRPAARRWGKCGPLCTRENIMVAFKGVWTQAFWKAVTAEFLAMLIFVL

LSLGSTINWGGMEKPLPVDMVLISLCFGLSIATMVQCFGHISGGHINPAV

TVAMVHGNLTAGHGLITFQLVFTIFASCDSKRTDVTGSIALAIGFSVAIG

HLFAINYTGASMNPARSFGPAVIMGNWENHWIYWVGPIIGAVLAGGLYEY

VFCPDAELKRRLKEAFSKAAQQTKGSYMEVEDNRSQVETEDLILKPGVVH

VIDIDRGEEKKGKDPSGEVLSSV.
```

SEQ ID NO:1 is encoded by the following DNA sequence:

```
                                             (SEQ ID NO: 2)
atgagcgatcgcccggcggcgcgccgctggggcaaatgcggcccgctgtg cacccgcgaaaacattatggtggcgtttaaaggcgtgtggacccaggcgt tttggaaagcggtgaccgcggaatttctggcgatgctgattttttgtgctg ctgagcctgggcagcaccattaactggggcggcatggaaaaaccgctgcc ggtggatatggtgctgattagcctgtgctttggcctgagcattgcgacca tggtgcagtgctttggccatattagcggcggccatattaacccggcggtg accgtggcgatggtgcatggcaacctgaccgcgggccatggcctgattac ctttcagctggtgtttaccattttgcgagctgcgatagcaaacgcaccg atgtgaccggcagcattgcgctggcgattggctttagcgtggcgattggc catctgtttgcgattaactataccggcgcgagcatgaacccggcgcgcag ctttggcccggcggtgattatgggcaactgggaaaaccattggatttatt gggtgggcccgattattggcgcggtgctggcgggcggcctgtatgaatat gtgttttgcccggatgcggaactgaaacgccgcctgaaagaagcgtttag caaagcggcgcagcagaccaaaggcagctatatggaagtggaagataacc gcagccaggtggaaaccgaagatctgattctgaaaccgggcgtggtgcat
```

-continued
```
gtgattgatattgatcgcggcgaagaaaaaaaaggcaaagatccgagcgg cgaagtgctgagcagcgtgagcatgagcgtgattaaaagccataacgtg.
```

Variants of SEQ ID NO: 1 are encoded by variants of SEQ ID NO: 2 (where such variants include all degenerate DNA sequences which encode specific variants of SEQ ID NO: 1).

The fluorescent reporter domain peptide includes a fluorescent domain comprising a sequence at least 70%, 80%, 90%, 95%, 98%, or 99% identical to:

```
                                          (SEQ ID NO: 3)
MYTDCKEFSNTYHNLGRLPDEDRHWSASCHHHHHMGMSGSSMSV

IKSHNVMVSKGEELFTGVVPILVELDGDVNGHKFSVRGEGEGDATNGKLT

LKFICTTGKLPVPWPTLVTTFGYGVACFSRYPDHMKQHDFFKSAMPEGYV

QERTISFKDDGTYKTRAEVKFEGDTLVNRIELKGIDFKEDGNILGHKLEY

NFNSHYVYITADKQKNSIKANFKIRHNVEDGSVQLADHYQQNTPIGDPV

LLPDNHYLSHQSKLSKDPNEKRDHMVLLEFVTAAGITLGMDELYKSGLRS

RAQASNSAVDGTAGPGSTGSR.
```

SEQ ID NO: 3 is encoded by a DNA sequence as follows:

```
                                          (SEQ ID NO: 4)
ATG TAT ACA GAC TGT AAG GAA TTC TCT AAT ACA TAT

CACAAT CTG GGG AGA CTT CCT GAT GAG GAC AGG CAC TGG

AGC GCC TCC TGC CAT CAT CAT CAT CAC CAT ATG GGG

ATG TCT GGCTCA TCT ATG AGC GTA ATC AAG TCC CAC AAT

GTC ATG GTG TCA AAA GGG GAA GAG TTG TTT ACC GGG

GTT GTT CCT ATT CTCGTA GAG TTG GAC GGT GAC GTG AAT

GGT CAC AAG TTC TCC GTT CGC GGC GAA GGA GAG GGT

GAT GCA ACC AAT GGG AAA CTGACC CTG AAA TTC ATA TGC

ACG ACT GGT AAA CTT CCT GTA CCG TGG CCG ACA CTC

GTT ACC ACG TTC GGG TAC GGA GTG GCTTGC TTC TCC AGA

TAC CCC GAC CAC ATG AAA CAA CAC GAC TTT TTC AAA

TCT GCA ATG CCC GAG GGC TAT GTT CAG GAA CGGACC ATA

TCT TTT AAG GAT GAT GGA ACA TAT AAA ACA AGG GCA

GAA GTA AAA TTT GAA GGG GAT ACT TTG GTG AAC AGG

ATAGAG CTC AAA GGG ATA GAT TTT AAG GAG GAC GGA AAT

ATA CTG GGC CAT AAG CTT GAG TAT AAT TTC AAC TCA

CAC TAC GTCTAT ATT ACA GCT GAC AAA CAA AAG AAC

AGT ATC AAA GCG AAC TTC AAG ATT CGC CAT AAT GTC

GAA GAT GGA AGC GTG CAACTC GCC GAC CAT TAT CAG CAG

AAC ACT CCG ATA GGC GAT GGA CCA GTA CTT CTG CCC

GAC AAC CAC TAT TTG AGT CAC CAGAGT AAG TTG AGT AAG

GAC CCT AAC GAG AAG AGA GAT CAC ATG GTC TTG CTC

GAA TTT GTG ACT GCA GCG GGT ATT ACC TTGGGA ATG GAC

GAG CTT TAC AAG TCT GGT CTT AGA TCA CGA GCA CAG

GCT TCA AAT TCT GCA GTA GAT GGT ACA GCC GGA CCCGGG

AGC ACA GGT TCT AGG TAA.
```

Variants of SEQ ID NO: 3 are encoded by variants of SEQ ID NO: 4 (where such variants include all degenerate DNA sequences which encode specific variants of SEQ ID NO: 3).

The invention also includes a nucleic acid construct encoding any of the osmolarity sensors described herein, and can include a tag sequence including: a nucleus localization signal (NLS) tag, a mitochondrial localization tag, and a ciliary tag. Further, the nucleic acid construct can include a sequence encoding the NLS tag or a sequence with at least 80% identity to the NLS tag peptide sequence: DPKKKRKV (SEQ ID NO: 5).

The invention includes a mammalian cell, preferably a human cell, comprising the osmolarity sensor described herein. In preferred embodiments, the human cell is an iPSC derived cell. For example, the cell can be derived from induction of a fibroblast or a blood cell to a pluripotent or immortal status. The cell is preferably derived from a human patient derived cell type.

The invention also includes methods of reprogramming and monitoring cells. For example, in a method of reprogramming fibroblasts can include transforming the fibroblasts with one or more constructs comprising a human clock gene and human Bmal1/2/3/4 genes having E-box promoters, synchronizing the circadian rhythm of the fibroblasts, modifying transcriptional regulatory control of the fibroblasts (thereby converting them into inducible pluripotent stem cells), and reprogramming the stem cells into inducible neurons (iN), glial cells, including astrocytes (iG), inducible pluripotent stem cells (iPSCs), or inducible neural progenitor cells (iNPCs). In many of the methods for reprogramming using circadian rhythms of human cell types, the transforming construct comprises a nucleic acid encoding an osmolarity sensor described herein.

The methods can include, e.g., modifying transcriptional control by providing specific transcription factors suitable for a lineage of the fibroblasts. The transcription factors can include the factors specific for a cellular lineage of the fibroblasts modified to include a circadian regulatory element (E-box promoters, an artificial E-box-like promoter sequence tag, a chemical agent that alters or synchronizes circadian rhythms cycles, or a synthetic transcriptional enhancer element) for reprogramming using circadian rhythms of human cell types.

The cellular composition can further include the co-culturing iN cells and iG cells to create a 2D monolayer or a 3D spheroid or organoid model, including on a scaffold in vitro. Cancer cell lines and cancer stem cells can be cultured in such 2D or 3D models using standard culturing hardware and conditions. Biosensor constructs of the invention can be used to image the resultant tissues and monitor changes in osmolarity in real time.

The present inventive methods include compositions and techniques for identifying, confirming or screening agents that influence osmolarity levels of cells. For example, methods for screening active agents can include transforming one or more cells with a nucleic acid encoding an osmolarity sensor, expressing the osmolarity sensor in the cells, contacting the cells with candidate active agents, and detecting a change in florescence of the sensor in response to the agent. Typical agents can include, e.g., members of a small molecule chemical library. For example, the agents can be reviewed for an activity resulting from interactions with a chloride ion channel, a receptor, and/or associated signaling pathways.

The methods herein are also useful in imaging live cells in low, medium, and/or high throughput assay formats. For example, cells in 3D arrays, transformed and expressing biosensor constructs of the invention can be viewed in real time, e.g., using microscopic imaging systems. Optionally, biosensor cells in surface or suspension culture can be monitored by detecting fluorescence changes (using monitors made by Molecular Devices, BioTek, or Tecan), confocal imaging or microscopes (including those made by Zeiss, Leica, Nikon, and Olympus), FACS sorters, CCD video imaging, and/or high content imagers (including: GE InCell 2000/6000, PerkinElmer Operetta, and EssenBioscience IncuCyte).

3D cancer cell models have been used as an improved predictor of tumor responses to drug candidates using library screening high throughput screening (HTS) methods. Cells used for such studies aren't limited to immortalized cancer cell lines. Neurons, cancer stem cells, primary tissue cells, and 3D printed tissue types can also be used for screening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

As used in this specification and the appended claims, the singular forms "a", "an" and "the" include plural references unless the content clearly dictates otherwise. Thus, for example, reference to "a surface" includes a combination of two or more surfaces; reference to "DNA" "peptide" "protein" "compound" includes, respectively, multiple individual molecules, and the like.

iPSC refers to inducible pluripotent stem cells; iN refers to inducible neurons; iG refers to inducible glial cells (including astrocytes); and iNPCs inducible neural progenitor cells.

Near-Infrared refers to light wavelengths ranging from about 600 nm to about 1400 nm.

The term "conservative variant" includes modifications of given sequences that result in conserved function. For example, in the context of nucleic acids, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

Similarly, conservative variants in the context of peptide sequences can be expected to retain function. For example, Guo, "Protein Tolerance to Random Amino Acid Change", (PNAS 101:9205-10; 2004), demonstrates that one of skill can modify peptides successfully even "without detailed knowledge of the ways in which a protein's structure relates to its functional usefulness . . . " Guo finds only 25% of random mutations lead to substantial loss of activity. Guo extensively discusses how one of skill can take into consideration active site location, alpha helices, beta sheets, hydrophobic interactions, turns and loops, conserved sites and the like to intelligently avoid loss of activity, e.g., by substitution avoidance at key positions or with conservative amino acid substitutions. Further, Guo states that his "database can be a valuable resource for predicting the effects of mutations on protein function . . . " Substitutions to known structures are predictable and in possession the of those having the structural information. Therefore, conservative amino acid substitutions, in which one or a few amino acids in an amino acid sequence are substituted with different amino acids with highly similar properties, are also readily identified as being highly similar to a disclosed constructs, and expected to retain function. One of skill will recognize that individual substitutions, deletions, or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

TABLE 1

Conservative Substitution Groups

| | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Trytophan (W) | |

The present invention includes biosensor constructs, preparing cells useful in receiving the constructs, cells transformed with the constructs, and assay methods employing the biosensors, e.g., to detect the presence of active agents or signals in living cells.

The biosensors generally include various complementary domain structures working together to sense osmolarity at a particular intracellular location, and to provide a distinct signal correlated to changes in the parameter. In a particularly useful embodiment, the biosensors are expressed in cells representative of a particular species (e.g., human), cell type of interest, or in a cell expressing a pathology of interest. Cells expressing the biosensors can be exposed to conditions or agents and monitored for signals indicating cell responses.

Biosensors Generally.

Biosensors of the present invention are generally engineered to include components specialized in providing, e.g., location, sensing, and reporting. In expression of a sensor nucleic acid construct, the peptide product can be positioned within the cell, e.g., by chaperone or transit sequences, hydrophobic affinities, or ligand/receptor interactions. The sensing domains typically change conformation in response to a changed intracellular condition or binding of a signal ion or molecule. Reporting domains typically present a detectable signal that changes in response to conformational changes in the associated sensing domain.

The intracellular location of a biosensor can optionally be controlled by a targeting domain or "tag." In some biosensors, intracellular location is generalized or passively determined. For example, the sensor may be generally dispersed throughout the nucleus and/or cytoplasm. In other cases, the function or specificity of the biosensor signal may depend on localization at a particular intracellular membrane or organelle. Localizing biosensor tags can be done using hydrophobic peptides which interact with membranes, ionic peptides which disperse in cytoplasm, and/or other chaperone sequences directing the biosensor to a particular compartment including ligands directed to receptors. Tags useful in the study of intracellular signaling and in agent screening assays can include, e.g., NLS tags, lipid membrane tag, endoplasmic reticulum (ER) tags, golgi tags, endosome tags, ciliary tags, and others.

Sensing domains in the biosensors change conformation in response to a changed osmolarity, whether caused by, binding of a ligand (peptide or nucleic acid), or a change in an ionic environment, caused, e.g., by interaction with a protease, interaction with a phosphatase, changes in pH, changes in ionic strength, or changes in a voltage potential. The conformational changes can, e.g., cause conformational changes in an associated reporter domain, or reposition the reporter domain to enhance or diminish the signal.

Reporter domains of the biosensors can be of any appropriate type known in the art. However, in preferred embodiments, the reporters comprise one or more peptide domains, e.g., so they can be readily employed in in vivo systems. Typically the peptide reporter domain provides a specific fluorescent emission in response to a specific interrogating excitation wavelength of light. In the context of sensor domain conformational changes, FRET strategies can be effective, e.g., wherein the biosensor construct comprises paired donor/acceptor peptide pairs. In certain embodiments, the reporter domain is adapted to provide an emission in the red to near-infrared spectrum, to allow the signal to pass and be detected in three dimensions through cells or tissue layers. For example, relatively penetrating reporter emission signals can range from 500 nm to 1400 nm, 550 nm to 900 nm, 600 nm to 850 nm, or 500 nm to 800 nm. In the 500 nm-800 nm range, the fluorescent properties can be easily changed to a point within that range, e.g. ~625 nm emission.

In an exemplary embodiment, the reporter domain includes fluorescence enhancing amino acids, such as tryptophan, tyrosine, phenylalanine, which contribute to their intrinsic fluorescence of the domain. Optionally, the reporter domain can include regions naturally modified post-translationally to provide the desired long wavelength emissions. For example, a domain that emits in the red regions can be a modified green fluorescent protein where the fluorophore originates from an internal serine-tyrosine-glycine sequence which is modified to a 4-(p-hydroxybenzylidene)-imidazolidin-5-one structure.

Biosensor constructs can include, e.g., two, three, or four of the above described domain types, in any of a variety of functional configurations. For example, a sensor domain and reporter domain in any order can constitute a biosensor. Often, the biosensors of the invention include at least three domains, e.g., a targeting domain, a sensor domain, and a reporting domain. The three domains can be in any order, but typically the targeting domain is on one end of the construct, the sensor in the middle and the reporter on the second end. In certain configurations, the biosensor construct can be in the order (C-terminal/N-terminal or N-terminal/C-terminal) of: sensor/reporter; targeting/sensor/reporter; targeting/reporter/sensor; targeting/reporter1/sensor/reporter2 (e.g., FRET); reporter1/sensor/reporter2; sensor/reporter1/reporter2; and targeting/sensor/reporter1/reporter2.

Typically, the domains are linked together in a commonly translated construct of a single linear peptide. Optionally, the constructs can include one or more domains not in the same peptide chain as another domain. For example, separate domains may be associated in a non-covalent interaction, such as a hydrophobic interaction, a chelation, a ligand/receptor interaction, an antibody/antigen interaction, and/or the like.

In some cases, a single domain may have more than one function. For example, a sensor domain may also have a structure functioning as a targeting domain. In one embodiment, a domain may have a series of transmembrane domains, acting as both as a sensor (e.g., ligand responsive ion channel) and a membrane specific targeting domain. In another aspect, a sensor domain could also include a reporter function, e.g., acting as a donor or quencher member of a FRET pair with a separate reporter domain.

Osmolarity Sensing Biosensors.

Osmolarity sensor constructs of the invention include many of the aspects described above for biosensors generally, but the sensor domain is responsive to changes in osmolarity. For example, the osmolarity sensor's conformation will change to some degree depending on the local osmolarity. Osmolarity can vary dramatically depending on cell type, condition, and the influence of induced signals. In living cells, osmolarity levels often vary with intracellular locations. The present osmolarity sensors can include targeting domains directing the sensors to any intracellular compartment of membrane, such as, e.g., a vacuole, the nucleus, cytoplasm, synapse, endoplasmic reticulum, and/or elsewhere.

All that is necessary for the osmolarity sensor role is that the peptide, or peptide fragment, changes conformation with changes in osmolarity. The change in conformation will translocate the reporter group and typically change the emission profile or intensity. Modern protein engineering techniques can be used to engineer enhancements causing the translocation of the reporter to be enhanced or quenched, e.g., by induced contact or induced conformational changes in the reporter itself.

A preferred osmolarity biosensor construct includes a combination of a tandem array of osmolarity binding domains and a fluorescent peptide. In an exemplary embodiment, the osmolarity sensor includes a modified osmolarity sensor domain derived from a known osmolarity sensor domain, and a fluorescent protein modified to provide red emissions. The domains of the constructs are typically configured from a combination of bioinformatics/database sequences as modified evolutionary mutagenesis.

SEQ ID NO: 1 is an osmolarity sensing domain. Conservative variations of SEQ ID NO: 1 would be expected to retain substantial sensing function. The present osmolarity sensing domains include peptides comprising sequences at least 70%, 80%, 85%, 90%, 95%, 98%, or 99% identical to SEQ ID NO: 1. SEQ ID NO: 3 is a particular reporter domain for the osmolarity sensor peptide. Conservative variations of SEQ ID NO: 3 would be expected to retain substantial useful function. The present fluorescent reporter sensor domains include peptides comprising sequences at least 70%, 80%, 85%, 90%, 95%, 98%, or 99% identical to SEQ ID NO: 3.

Biosensor Constructs in Human Cells.

The biosensors described herein can be incorporated into mammalian cells to monitor chloride ion conditions within the cells. For example, nucleic acid constructs encoding the biosensor peptide domains can be transformed or transfected into eukaryotic cells for expression, e.g., using appropriate promoters, as is known in the art. The cells can be mammalian, preferably human, providing the benefit of a reliable host cell model, e.g., for study of human signal transduction and disease states. The mammalian cells can be immortalized, but are preferably stem cells or cells induced to be pluripotent, or cells induced or otherwise differentiated to become a particular cell type of interest.

The nucleic acid construct can encode any biosensor described herein. For example, the construct can encode a combination of a osmolarity sensor domain, a targeting domain, and/or a reporter domain. In one embodiment, the nucleic acid construct includes transient expression vector components directing expression of peptide chains comprising a combination of domains providing a functional biosensor. For example, the nucleic acid can express a single peptide chain comprising a combination of osmolarity sensor domain, troponin domain, and reporter domain. In another example, the nucleic acid construct can encode a peptide comprising at least a combination of a transmembrane domain, an osmolarity sensing domain, and reporter domain.

In other embodiments of the nucleic acid expression constructs, an expression vector includes sequences encoding peptides of any of SEQ ID NOs: 1, 3, or 5. In certain embodiments functioning as osmolarity biosensors, the vector can include a combination of nucleic acid sequences encoding the peptides of SEQ ID NOs: 1 and 3, e.g., along with a sequence encoding a transmembrane domain, such as an ion channel domain. Such a construct can encode functional peptide sequences at least 70%, 80%, 85%, 90%, 95%, 98%, or 99% identical to the sequence of SEQ ID No: 1 and/or SEQ ID NO: 3. The cells transformed with TempoOsmo™ used in the experiments shown in FIGS. 1 to 3, were transformed with nucleic acid sequences encoding (C to N terminus) the peptides of SEQ ID NO: 1 and SEQ ID NO: 3, i.e., these cells were transformed using vectors including SEQ ID NOs: 2 and 4.

Useful nucleic acid constructs of the above expression vectors can include additional sequences encoding targeting tags, such as, e.g., a NLS tag, a lipid membrane tag, an ER tag, a golgi tag, an endosome tag, a mitochondrial tag, and/or a ciliary tag. For example, the targeting tag can include a sequence at least 70%, 80%, 85%, 90%, 95%, 98%, or 99% identical to a sequence encoding the peptide tag sequence of SEQ ID NO: 5.

The present inventions include cells comprising the biosensors discussed herein. For example, nucleic acid constructs coding the biosensor peptides can be transduced or transfected into eukaryotic cells of choice. In preferred embodiments, the cells originate from a mammal, preferably from a human. In many embodiments, the cell is an immortalized stem cell, or a cell fully or partially differentiated from a stem cell.

In the context of the present biosensors, cells can be initially derived from patient samples. The advantage of such cells is that they can provide very representative responses to active agents and changed conditions for that patient. Thus, such cell models are more likely to provide information on the modes of action or efficacy of a candidate therapeutic for that patient. For example, such cell models can aid in the identification of custom tailored treatment for patients with certain disease states, such as autoimmune diseases, neurological diseases, cancer, diabetes, or pathologies from genetic flaws.

Alternately, the models can employ cells harboring a particular non-endogenous gene of interest, introduced by genetic engineering techniques. For example, the gene of interest can encode a receptor molecule, a G-protein coupled receptor, or an ion channel of interest. Typically, the host cell is a cell most representative of the cell type of interest in the research. Such model cells can be useful in providing more representative results, e.g., in monitoring a signal transduction or in screening prospective agents active in the modulation of the gene of interest.

Cellular models can be derived from inducible cells available from primary culture of cells from living animals. For example, fibroblasts or undifferentiated cells from circulating blood can be induced to provide pluripotent cells. It is notable that epigenetic processes can play a key role in directing the status of a cell to stem cell, progenitor cell, or mature cell. In Lister (Nature 471 (7336): 68-73, 2011), aberrant epigenomic programming was found capable of inducing a variety of different pluripotent stem cells (iPSCs). Female lung fibroblasts, adipose cells, and foreskin fibroblasts were reprogrammed into induced pluripotent state using OCT4, SOX2, KLF4, and MYC genes. The iPSCs were found to be similar to embryonic stem cells in many characteristics, including DNA methylation patterns. Such concepts can be used to reprogram cells, e.g., in combination with further circadian synchronization techniques, described below.

In addition to inducement by action of immortalizing genes, cell signaling was found to influence epigenetic processes governing differentiation. In the research of Baylin (e.g., Nature Biotechnology 28 (10): 1033-8, 2010), several signaling pathways were suggested as important in the induction and maintenance of embryonic stem cells and in their differentiation. For example, signaling pathways of growth factors can play a role in epigenetic regulation of cellular differentiation. These growth factors include, e.g., transforming growth factors (TGFs), fibroblast growth factors (FGFs), and bone morphogenetic proteins. Another important factor in induction and differentiation can be the Wnt signaling pathway.

Circadian rhythm influences on cellular synchronization can be employed in inducement of pluoripotential cells. For example, cells can be reprogrammed into inducible pluripotent stem cells using human clock gene and human Bmal1/2/3/4 genes and their E-box promoters. In one aspect, fibroblast iPSCs can be generated by such reprogramming, and further directed to provide inducible neurons (iN), glial cells, or inducible neural progenitor cells (iNPCs), as desired. The reprogramming factor for each cell type is typically a transcriptional regulator that is specific for the cellular lineage. Each factor can be modified to be controlled by a circadian regulatory element (such as, E-box promoters or an artificial E-box-like promoter sequence tag). Such promoter sequences can be added to each transcriptional regulator, thus forming a novel transcriptional element for control regulated by human Clock and Bmal genes.

To complement the biosensor systems described herein, induced cells can be cultured together in a "tissue" structure, e.g., in three dimensions. In this way, the cell to cell contacts of interest can be studied, e.g., using penetrating imaging available in the form of near infrared reporter signals. For example, co-cultures of iN and iG can be prepared to create a 3D model of a neuronal structure. The structure can be further controlled, e.g., using an appropriately structured scaffold, e.g., using materials not opaque to reporter signals, e.g., for confocal microscopic review.

Screening and Assay Methods Using Biosensors in Model Cells

The biosensor constructs, e.g., engineered into model cells of interest, can more predictably provide assay and screening results relevant to life science research and study of clinical pathologies of interest. That is, the present targeted biosensors in appropriate cell types, differentiated to a particular phenotype, can provide models more likely to anticipate a normal response in the modeled organism than, e.g., old art xenotypic models.

The initial steps in preparing a model system can be to identify the cell type of interest and the signal to be detected. For example, to study certain potential therapeutic agents, one may choose to examine osmolarity changes with an osmolarity sensor. Typically the biosensor constructs are transiently expressed in the cells using, e.g., a CMV constitutive promoter or a cell-type-specific promoter.

Once the model system is established, the biosensor can be monitored in a single cell, or across an array of cells. For example, a cell can be exposed to a signaling agent to see if the cell type responds to that agent, e.g., a cytokine or candidate small molecule bioactive agent. Optionally, the cell can be co-transfected with a second expression construct of a peptide of interest (e.g., a tumor-associated antigen or oncogene) to monitor any influence of the external gene in a signaling pathway.

In other embodiments, the cells can be segregated into arrays complementary to low, medium, or high throughput assay formats. For example, cells can be dispensed into 96-well plates, onto a micro-well array, or a FACS sorter, for separate exposure to library members of putative candidate agents. Such arrays can be reviewed suing standard fluorescent detection equipment. Optionally, the arrays can be reviewed photographically with digital CCD based cameras. Changes in a signal, e.g., as compared to a positive or negative reference, can be flagged for additional characterization.

Targeting Tags

In many cases, it is advantageous to direct the osmolarity sensor to a particular intracellular membrane or compartment. The biosensors of the invention can include peptide segments adapted to have an affinity for a cellular target.

Exemplary peptide sequences useful in targeting biosensors to a desired intracellular location include, e.g.:

```
NLS tag (protein sequence):
                                          (SEQ ID NO: 5)
DPKKKRKV.

ER tag:
                                          (SEQ ID NO: 6)
KDEL

Endosome tag:
                                          (SEQ ID NO: 7)
NPTY--DXXLL--YXXoo (protein sequence; tandem
motifs; oo = 2 two residues with hydrophobic side
groups;

Ciliary tag:
                                          SEQ ID NO: 8
VxPx-RVxP-KVHPSST-AxEGG (protein sequence; tandem
motifs)
```

```
Human endosome sequence tag
                                          (SEQ ID NO: 9)
MTSRKKVLLKVIILGDSGVGKTSLMHRYVND human synapsin tag:
                                          SEQ ID NO: 10
CCTGCAGGGCCCACTAGTATCTGCAGAGGGCCCTGCGTATGAGTGCAAG

TGGGTTTTAGGACCAGGATGAGGCGGGGTGGGGGTGCCTACCTGACGAC

CGACCCCGACCCACTGGACAAGCACCCAACCCCCATTCCCCAAATTGCG

CATCCCCTATCAGAGAGGGGGAGGGGAAACAGGATGCGGCGAGGCGCGT

GCGCACTGCCAGCTTCAGCACCGCGGACAGTGCCTTCGCCCCCGCCTGG

CGGCGCGCGCCACCGCCGCCTCAGCACTGAAGGCGCGCTGACGTCACTC

GCCGGTCCCCCGCAAACTCCCCTTCCCGGCCACCTTGGTCGCGTCCGCG

CCGCCGCCGGCCCAGCCGGACCGCACCACGCGAGGCGCGAGATAGGGGG

GCACGGGCGCGACCATCTGCGCTGCGGCGCCGGCGACTCAGCGCTGCCT

CAGTCTGCGGTGGGCAGCGGAGGAGTCGTGTCGTGCCTGAGAGCGCAGC

TGTGCTCCTGGGCACCGCGCAGTCCGCCCCCGCGGCTCCTGGCCAGACC

ACCCCTAGGACCCCCTGCCCCAAGTCGCAGCC

Human synaptic vesicle tag:
                                          SEQ ID NO: 11
MDCLCIVTTK KYRYQDEDTP PLEHSPAHLP NQANSPPVIV NTDT

LEAPGYELQVNGTEGE MEYEEITLER GNSGLGFSIA GGTDNPHIG

D DPSIFITKIIPGGAAAQDGR LRVNDSILFV NEVDVREVTH SAAV

EALKEA GSIVRLYVMRRKPPAEKVME IKLIKGPKGL GFSIAGGVG

N STSLEITASM
```

EXAMPLES

Figure 1:
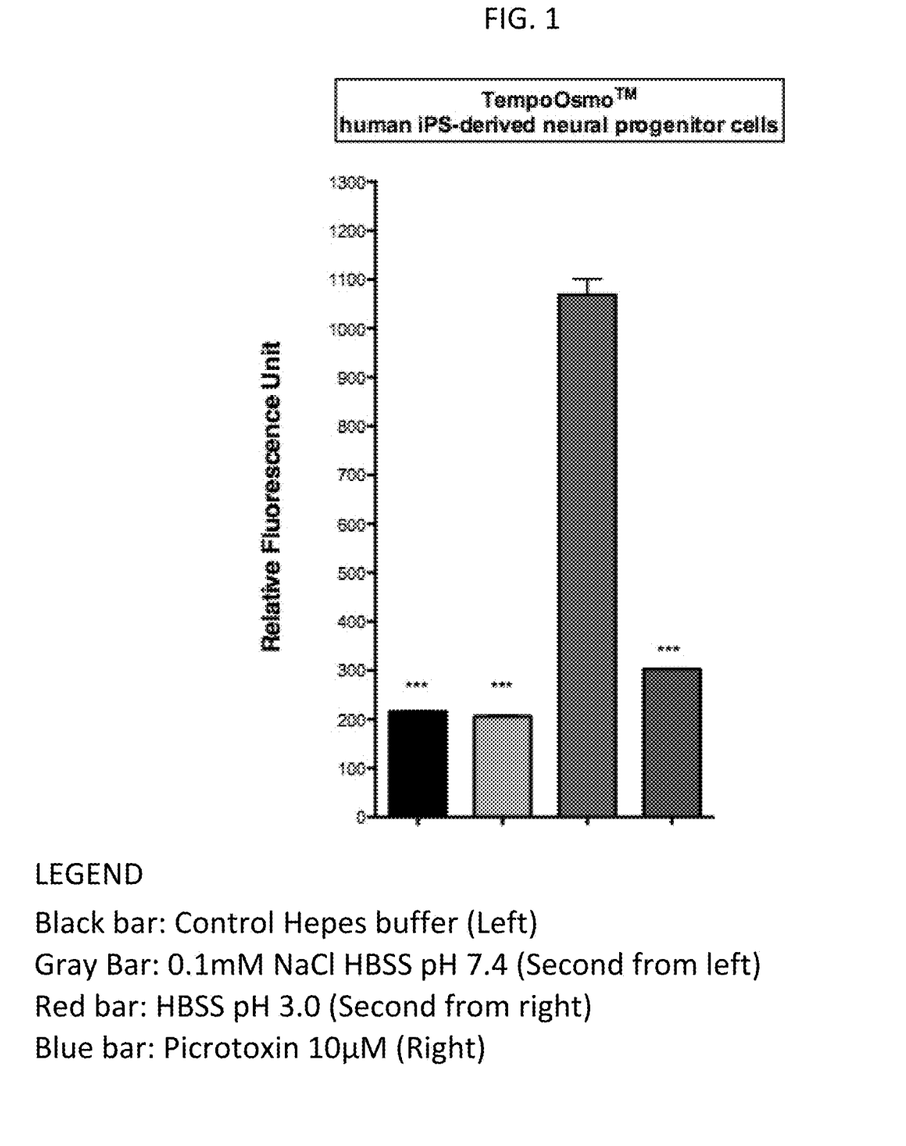
FIG. 1 shows sample identification with the TempoOsmo™ biosensor, which is pH sensitive, expressed in human iPS-derived neural progenitor cells, where detection is based on relative fluorescence.

FIG. 1 shows the TempoOsmo™ biosensor, which is pH sensitive (expressed in transformed neural human IPS progenitor cells) successfully identifying a sample of HBSS buffer at pH 3.0 based on relative fluorescence against the other sample solutions which are pH 7.4; i.e., control HEPES Buffer has pH 7.4 and osmolarity at standard mOsm=300 (+/−15); 0.1 mM NaCl is in 1×HBSS buffer, pH 7.4; and 10 microMolar Picrotoxin is also in 1×HBSS buffer pH 7.4. The fluorescence detection parameters were: 517 nm Excitation/535 nm Emission (+/−2).

Picrotoxin, also known as cocculin, is a poisonous crystalline plant compound which has been shown to inhibit neurotransmitter GABA-ergic ion channels; acting, in vivo, as a plant-derived stimulant and convulsant. See, Newland, C F; Cull-Candy, S G (February 1992). "On the mechanism of action of picrotoxin on GABA receptor channels in dissociated sympathetic neurones of the rat". The Journal of Physiology. 447: 191-213. doi:10.1113/jphysiol.1992.sp018998. PMC 1176032 Freely accessible. PMID 1317428.

Figure 2:
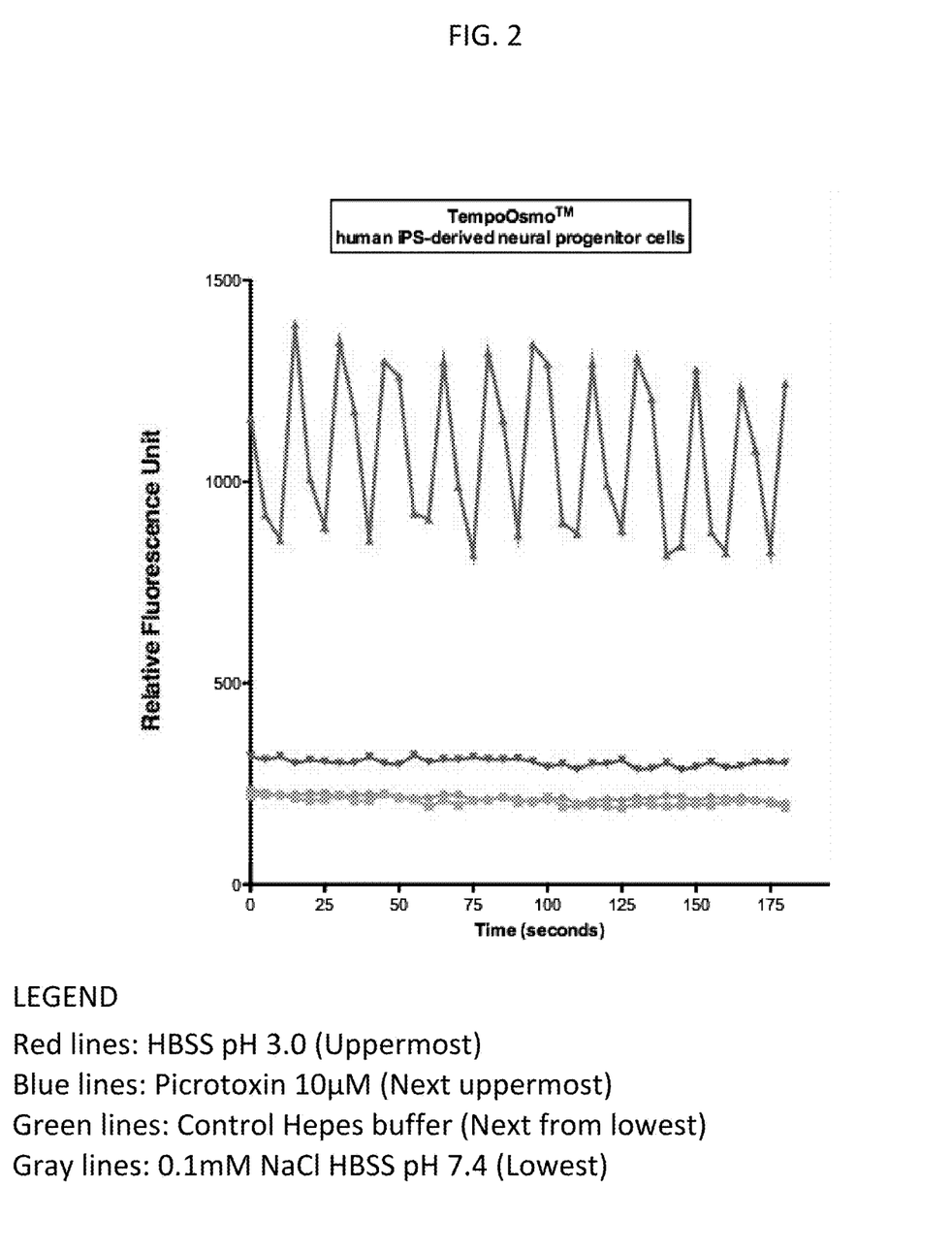
FIG. 2 shows sample identification with the TempoOsmo™ biosensor, expressed in human iPS-derived neural progenitor cells, where detection is based on relative fluorescence.

FIG. 2 shows the TempoOsmo™ biosensor (expressed in transformed neural human IPS progenitor cells) successfully identifying a sample of HBSS buffer at pH 3.0, based on relative fluorescence against other samples which are at pH 7.4, as determined by kinetic readouts (X axis shows: seconds per scan). The fluorescence detection parameters were: 517 nm Excitation/535 nm Emission (+/−2).

Figure 3:
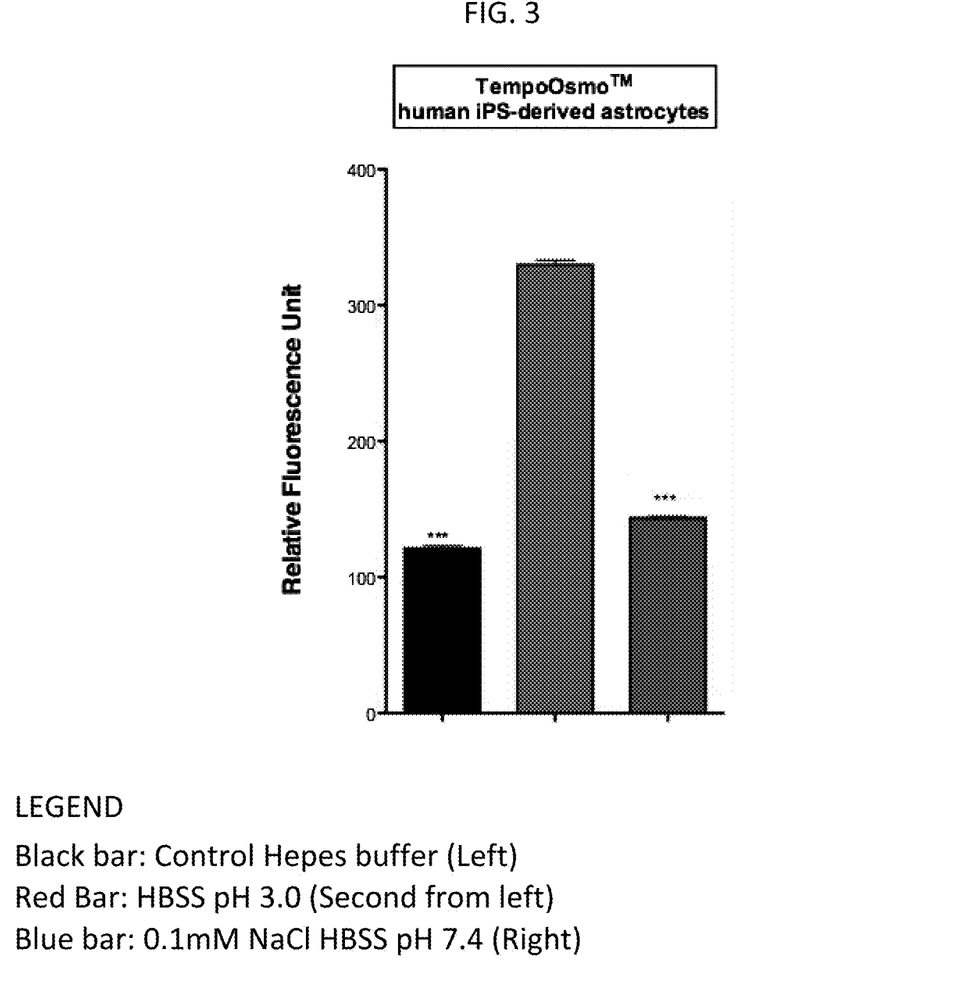
FIG. 3 shows sample identification with the TempoOsmo™ biosensor, expressed in human iPS-derived astrocytes, where detection is based on relative fluorescence.

FIG. 3 shows the TempoOsmo™ biosensor (expressed in transformed human iPS-derived astrocytes, which are glial cells) successfully identifying a sample of HBSS buffer at pH 3.0, based on relative fluorescence against other samples which are at pH 7.4.

It can be seen, therefore, that the TempoOsmo™ biosensor system is effective in detecting chloride ions in divergent cell types, including neurons and glial cells, and would be effective in other mammalian or human cell types, including, immortalized, native or induced: pluripotent stem cells, neurons, glial cells, and neural progenitor cells.

The specific methods, procedures and apparatus described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An osmolarity sensor peptide construct comprising: an osmolarity sensing domain having the amino acid sequence set forth in SEQ ID NO: 1; and, a fluorescent reporter, wherein the fluorescent reporter is adapted to fluoresce at wavelengths in the range from 500 nm to 1400 nm; wherein the fluorescent reporter is adapted to change fluorescent emissions characteristics in response to osmolarity changes.

2. The osmolarity sensor peptide construct of claim 1, wherein the fluorescent reporter has a fluorescent emission range of 500 nm to 700 nm and a fluorescent excitation range of 400 nm to 700 nm.

3. The osmolarity sensor peptide construct of claim 1, wherein the fluorescent reporter comprises the amino acid sequence set forth in SEQ ID NO: 3.

* * * * *

SEQUENCE LISTING

```
<160> NUMBER OF SEQ ID NOS: 11

<210> SEQ ID NO 1
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Asp Arg Pro Ala Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Met Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val His Gly Asn Leu Thr Ala Gly
            100                 105                 110

His Gly Leu Ile Thr Phe Gln Leu Val Phe Thr Ile Phe Ala Ser Cys
        115                 120                 125

Asp Ser Lys Arg Thr Asp Val Thr Gly Ser Ile Ala Leu Ala Ile Gly
    130                 135                 140

Phe Ser Val Ala Ile Gly His Leu Phe Ala Ile Asn Tyr Thr Gly Ala
145                 150                 155                 160

Ser Met Asn Pro Ala Arg Ser Phe Gly Pro Ala Val Ile Met Gly Asn
                165                 170                 175
```

Trp Glu Asn His Trp Ile Tyr Trp Val Gly Pro Ile Ile Gly Ala Val
            180                 185                 190

Leu Ala Gly Gly Leu Tyr Glu Tyr Val Phe Cys Pro Asp Ala Glu Leu
        195                 200                 205

Lys Arg Arg Leu Lys Glu Ala Phe Ser Lys Ala Ala Gln Gln Thr Lys
    210                 215                 220

Gly Ser Tyr Met Glu Val Glu Asp Asn Arg Ser Gln Val Glu Thr Glu
225                 230                 235                 240

Asp Leu Ile Leu Lys Pro Gly Val Val His Val Asp Ile Asp Arg
                245                 250                 255

Gly Glu Glu Lys Lys Gly Lys Asp Pro Ser Gly Glu Val Leu Ser Ser
            260                 265                 270

Val

<210> SEQ ID NO 2
<211> LENGTH: 849
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgagcgatc gcccggcggc gcgccgctgg ggcaaatgcg gcccgctgtg caccgcgaa      60 aacattatgg tggcgtttaa aggcgtgtgg acccaggcgt tttggaaagc ggtgaccgcg     120
gaatttctgg cgatgctgat ttttgtgctg ctgagcctgg cagcaccat taactggggc     180 ggcatggaaa accgctgcc ggtggatatg gtgctgatta gcctgtgctt tggcctgagc     240
attgcgacca tggtgcagtg ctttggccat attagcggcg ccatattaa cccggcggtg     300 accgtggcga tggtgcatgg caacctgacc gcgggccatg gcctgattac ctttcagctg     360
gtgtttacca ttttgcgag ctgcgatagc aaacgcaccg atgtgaccgg cagcattgcg     420
ctggcgattg gctttagcgt ggcgattggc catctgtttg cgattaacta taccggcgcg     480
agcatgaacc cggcgcgcag ctttggcccg gcggtgatta tgggcaactg ggaaaaccat     540
tggatttatt gggtgggccc gattattggc gcggtgctgg cggcggcct gtatgaatat     600 gtgtttttgcc cggatgcgga actgaaacgc gccctgaaag aagcgtttag caaagcggcg     660
cagcagacca aaggcagcta tatggaagtg gaagataacc gcagccaggt ggaaaccgaa     720
gatctgattc tgaaaccggg cgtggtgcat gtgattgata ttgatcgcgg cgaagaaaaa     780
aaaggcaaag atccgagcgg cgaagtgctg agcagcgtga gcatgagcgt gattaaaagc     840
cataacgtg                                                              849

<210> SEQ ID NO 3
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Tyr Thr Asp Cys Lys Glu Phe Ser Asn Thr Tyr His Asn Leu Gly
1               5                   10                  15

Arg Leu Pro Asp Glu Asp Arg His Trp Ser Ala Ser Cys His His His
            20                  25                  30

```
His His His Met Gly Met Ser Gly Ser Ser Met Ser Val Ile Lys Ser
            35                  40                  45

His Asn Val Met Val Ser Lys Gly Glu Glu Leu Phe Thr Gly Val Val
 50                  55                  60

Pro Ile Leu Val Glu Leu Asp Gly Asp Val Asn Gly His Lys Phe Ser
 65                  70                  75                  80

Val Arg Gly Glu Gly Glu Gly Asp Ala Thr Asn Gly Lys Leu Thr Leu
                 85                  90                  95

Lys Phe Ile Cys Thr Thr Gly Lys Leu Pro Val Pro Trp Pro Thr Leu
                100                 105                 110

Val Thr Thr Phe Gly Tyr Gly Val Ala Cys Phe Ser Arg Tyr Pro Asp
                115                 120                 125

His Met Lys Gln His Asp Phe Phe Lys Ser Ala Met Pro Glu Gly Tyr
130                 135                 140

Val Gln Glu Arg Thr Ile Ser Phe Lys Asp Asp Gly Thr Tyr Lys Thr
145                 150                 155                 160

Arg Ala Glu Val Lys Phe Glu Gly Asp Thr Leu Val Asn Arg Ile Glu
                165                 170                 175

Leu Lys Gly Ile Asp Phe Lys Glu Asp Gly Asn Ile Leu Gly His Lys
                180                 185                 190

Leu Glu Tyr Asn Phe Asn Ser His Tyr Val Tyr Ile Thr Ala Asp Lys
                195                 200                 205

Gln Lys Asn Ser Ile Lys Ala Asn Phe Lys Ile Arg His Asn Val Glu
                210                 215                 220

Asp Gly Ser Val Gln Leu Ala Asp His Tyr Gln Gln Asn Thr Pro Ile
225                 230                 235                 240

Gly Asp Gly Pro Val Leu Leu Pro Asp Asn His Tyr Leu Ser His Gln
                245                 250                 255

Ser Lys Leu Ser Lys Asp Pro Asn Glu Lys Arg Asp His Met Val Leu
                260                 265                 270

Leu Glu Phe Val Thr Ala Ala Gly Ile Thr Leu Gly Met Asp Glu Leu
                275                 280                 285

Tyr Lys Ser Gly Leu Arg Ser Arg Ala Gln Ala Ser Asn Ser Ala Val
                290                 295                 300

Asp Gly Thr Ala Gly Pro Gly Ser Thr Gly Ser Arg
305                 310                 315

<210> SEQ ID NO 4
<211> LENGTH: 951
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgtatacag actgtaagga attctctaat acatatcaca atctggggag acttcctgat      60
gaggacaggc actggagcgc tcctgccat catcatcatc accatatggg gatgtctggc     120
tcatctatga gcgtaatcaa gtcccacaat gtcatggtgt caaaagggga agagttgttt     180
accggggttg ttcctattct cgtagagttg gacggtgacg tgaatggtca aagttctcc      240 gttcgcggcg aaggagaggg tgatgcaacc aatgggaaac tgaccctgaa attcatatgc     300
acgactggta aacttcctgt accgtggccg cactcgtta ccacgttcgg gtacggagtg      360
gcttgcttct ccagataccc cgaccacatg aaacaacacg acttttttcaa atctgcaatg    420
```

```
cccgagggct atgttcagga acggaccata tcttttaagg atgatggaac atataaaaca    480
agggcagaag taaaatttga aggggatact ttggtgaaca ggatagagct caaagggata    540
gattttaagg aggacggaaa tatactgggc cataagcttg agtataattt caactcacac    600
tacgtctata ttacagctga caaacaaaag aacagtatca aagcgaactt caagattcgc    660
cataatgtcg aagatggaag cgtgcaactc gccgaccatt atcagcagaa cactccgata    720
ggcgatggac cagtacttct gcccgacaac cactatttga gtcaccagag taagttgagt    780
aaggacccta acgagaagag agatcacatg gtcttgctcg aatttgtgac tgcagcgggt    840
attaccttgg gaatggacga gctttacaag tctggtctta gatcacgagc acaggcttca    900
aattctgcag tagatggtac agccggaccc gggagcacag gttctaggta a            951
```

```
<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Pro Lys Lys Lys Arg Lys Val
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Asp Glu Leu
1

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (13)..(14)
<223> OTHER INFORMATION: Any residue with a hydrophobic side group

<400> SEQUENCE: 7

Asn Pro Thr Tyr Asp Xaa Xaa Leu Leu Tyr Xaa Xaa Xaa Xaa
1               5                   10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (17)..(17)
<223> OTHER INFORMATION: Any amino acid

<400> SEQUENCE: 8

Val Xaa Pro Xaa Arg Val Xaa Pro Lys Val His Pro Ser Ser Thr Ala
1               5                   10                  15

Xaa Glu Gly Gly
            20

<210> SEQ ID NO 9
<211> LENGTH: 31
<212> TYPE: PRT
<213> ORGANISM: Homo sapiens

<400> SEQUENCE: 9

Met Thr Ser Arg Lys Lys Val Leu Leu Lys Val Ile Ile Leu Gly Asp
1               5                   10                  15

Ser Gly Val Gly Lys Thr Ser Leu Met His Arg Tyr Val Asn Asp
            20                  25                  30

<210> SEQ ID NO 10
<211> LENGTH: 571
<212> TYPE: DNA
<213> ORGANISM: Homo sapiens

<400> SEQUENCE: 10
cctgcagggc ccactagtat ctgcagaggg ccctgcgtat gagtgcaagt gggttttagg      60
accaggatga ggcggggtgg gggtgcctac ctgacgaccg accccgaccc actggacaag     120
cacccaaccc ccattcccca aattgcgcat cccctatcag agaggggag gggaaacagg      180 atgcggcgag gcgcgtgcgc actgccagct tcagcaccgc ggacagtgcc ttcgccccg      240 cctggcggcg cgcgccaccg ccgcctcagc actgaaggcg cgctgacgtc actcgccggt     300
cccccgcaaa ctccccttcc cggccacctt ggtcgcgtcc gcgccgccgc cggcccagcc     360
ggaccgcacc acgcgaggcg cgagataggg gggcacgggc gcgaccatct cgctgcggc     420 gccggcgact cagcgctgcc tcagtctgcg gtgggcagcg gaggagtcgt gtcgtgcctg     480
agagcgcagc tgtgctcctg ggcaccgcgc agtccgcccc cgcggctcct ggccagacca     540 ccctaggac cccctgcccc aagtcgcagc c                                    571

<210> SEQ ID NO 11
<211> LENGTH: 190
<212> TYPE: PRT
<213> ORGANISM: Homo sapiens

<400> SEQUENCE: 11

Met Asp Cys Leu Cys Ile Val Thr Thr Lys Lys Tyr Arg Tyr Gln Asp
1               5                   10                  15
```

```
Glu Asp Thr Pro Pro Leu Glu His Ser Pro Ala His Leu Pro Asn Gln
            20              25              30

Ala Asn Ser Pro Pro Val Ile Val Asn Thr Asp Thr Leu Glu Ala Pro
            35              40              45

Gly Tyr Glu Leu Gln Val Asn Gly Thr Glu Gly Glu Met Glu Tyr Glu
    50              55              60

Glu Ile Thr Leu Glu Arg Gly Asn Ser Gly Leu Gly Phe Ser Ile Ala
65              70              75              80

Gly Gly Thr Asp Asn Pro His Ile Gly Asp Asp Pro Ser Ile Phe Ile
            85              90              95

Thr Lys Ile Ile Pro Gly Gly Ala Ala Ala Gln Asp Gly Arg Leu Arg
            100             105             110

Val Asn Asp Ser Ile Leu Phe Val Asn Glu Val Asp Val Arg Glu Val
            115             120             125

Thr His Ser Ala Ala Val Glu Ala Leu Lys Glu Ala Gly Ser Ile Val
            130             135             140

Arg Leu Tyr Val Met Arg Arg Lys Pro Pro Ala Glu Lys Val Met Glu
145             150             155             160

Ile Lys Leu Ile Lys Gly Pro Lys Gly Leu Gly Phe Ser Ile Ala Gly
            165             170             175

Gly Val Gly Asn Ser Thr Ser Leu Glu Ile Thr Ala Ser Met
            180             185             190
```